US012678186B2

(12) United States Patent
Kefilev et al.

(10) Patent No.: US 12,678,186 B2
(45) Date of Patent: Jul. 14, 2026

(54) DEVICE AND METHOD FOR SKIN TREATMENT

(71) Applicant: BTL Healthcare Technologies a.s., Prague (CZ)

(72) Inventors: Radoslav A. Kefilev, Chepelare (BG); Tomáš Schwarz, Prague (CZ)

(73) Assignee: BTL Healthcare Technologies a.s., Prague (CZ)

( * ) Notice: Subject to any disclaimer, the term of this patent is extended or adjusted under 35 U.S.C. 154(b) by 0 days.

(21) Appl. No.: 18/299,189

(22) Filed: Apr. 12, 2023

(65) Prior Publication Data

US 2023/0329739 A1 Oct. 19, 2023

Related U.S. Application Data

(60) Provisional application No. 63/362,921, filed on Apr. 13, 2022.

(51) Int. Cl.
*A61B 17/32* (2006.01)
*A61B 17/00* (2006.01)

(52) U.S. Cl.
CPC .... *A61B 17/32* (2013.01); *A61B 2017/00761* (2013.01); *A61B 2017/320004* (2013.01)

(58) Field of Classification Search
CPC .................. A61B 17/54; A61B 17/545; A61B 2017/00752; A61B 2017/320004; A45D 2200/1054
See application file for complete search history.

(56) References Cited

U.S. PATENT DOCUMENTS

| | | | |
|---|---|---|---|
| 3,809,977 A | 5/1974 | Balamuth | |
| 3,828,770 A | 8/1974 | Kuris | |

(Continued)

FOREIGN PATENT DOCUMENTS

| | | | |
|---|---|---|---|
| WO | 2010132496 A1 | 11/2010 | |
| WO | 2020186502 A1 | 9/2020 | |

(Continued)

OTHER PUBLICATIONS

Edge Systems, LLC, Hydrafacial MD Elite User Guide, 12 pp, Feb. 2020.

(Continued)

*Primary Examiner* — Martin T Ton
(74) *Attorney, Agent, or Firm* — Riverside Law LLP

(57) ABSTRACT

The invention relates in general to the field of human skin treatment, more specifically to devices and methods for cleansing and subsequent care of a person's skin. The methods effectively use the combination of mechanical cleansing strengthened by vibrations transmitted to a tip, lowered pressure and treatment liquid. The advantageous aspect of the device according to the invention is that vibrations are transmitted from the vibration mechanism directly to at least a portion of the tip that is in contact with the patient's skin. This means that vibrations are targeted to the place of use, and the vibration of the whole applicator is, in comparison with methods and devices according to the state of the art, significantly lowered, as are occurrences of hand pain and other inconveniences for the person providing the therapy. The other advantageous aspect of the device is a special design of the applicator for reducing the risk of spilling serum when treatment is stopped or interrupted.

30 Claims, 11 Drawing Sheets

(56)  References Cited

U.S. PATENT DOCUMENTS

| | | | |
|---|---|---|---|
| 3,924,335 A | 12/1975 | Balamuth | |
| RE28,752 E | 3/1976 | Balamuth | |
| 3,980,906 A | 9/1976 | Kuris | |
| 5,150,492 A | 9/1992 | Suroff | |
| 5,378,153 A | 1/1995 | Giuliani | |
| 6,080,166 A * | 6/2000 | McEwen | A61B 17/322 |
| | | | 606/167 |
| 6,203,320 B1 | 3/2001 | Williams | |
| 6,241,739 B1 | 6/2001 | Waldron | |
| 6,299,620 B1 | 10/2001 | Shadduck | |
| 6,306,119 B1 | 10/2001 | Weber | |
| 6,387,103 B2 | 5/2002 | Shadduck | |
| 6,423,078 B1 * | 7/2002 | Bays | A61B 17/32 |
| | | | 606/131 |
| 6,500,183 B1 | 12/2002 | Waldron | |
| 6,503,256 B2 | 1/2003 | Parkin | |
| 6,527,783 B1 | 3/2003 | Ignon | |
| 6,582,442 B2 | 6/2003 | Simon | |
| 6,592,595 B1 | 7/2003 | Mallett | |
| 6,629,983 B1 | 10/2003 | Ignon | |
| 6,641,591 B1 | 11/2003 | Shadduck | |
| 6,673,082 B2 | 1/2004 | Mallett | |
| 6,695,853 B2 | 2/2004 | Karasiuk | |
| 6,726,693 B2 | 4/2004 | Weber | |
| 6,764,493 B1 | 7/2004 | Weber | |
| 6,911,031 B2 | 6/2005 | Muldner | |
| 6,918,153 B2 | 7/2005 | Gruber | |
| 6,926,681 B1 | 8/2005 | Ramey | |
| 6,942,649 B2 | 9/2005 | Ignon | |
| 7,264,026 B2 | 9/2007 | Gruber | |
| 7,320,691 B2 | 1/2008 | Pilcher | |
| 7,367,981 B2 | 5/2008 | Bernaz | |
| 7,384,405 B2 | 6/2008 | Rhoades | |
| 7,445,372 B1 * | 11/2008 | Engel | B01F 27/271 |
| | | | 366/195 |
| 7,658,742 B2 | 2/2010 | Karasiuk | |
| 7,678,120 B2 | 3/2010 | Shadduck | |
| 7,789,886 B2 | 9/2010 | Shadduck | |
| 7,837,695 B2 | 11/2010 | Hart | |
| 7,951,156 B2 | 5/2011 | Karasiuk | |
| 8,048,089 B2 | 11/2011 | Ignon | |
| 8,066,716 B2 | 11/2011 | Shadduck | |
| 8,128,638 B2 | 3/2012 | Karasiuk | |
| 8,221,437 B2 | 7/2012 | Waldron | |
| 8,236,008 B2 | 8/2012 | Boone, III | |
| 8,277,287 B2 | 10/2012 | Hart | |
| 8,337,513 B2 | 12/2012 | Shadduck | |
| 8,343,116 B2 | 1/2013 | Ignon | |
| 8,389,582 B2 | 3/2013 | Mitragotri | |
| 8,435,194 B2 | 5/2013 | Dverin | |
| 8,609,041 B2 | 12/2013 | Mitragotri | |
| 8,642,664 B2 | 2/2014 | Mitragotri | |
| 8,721,662 B2 | 5/2014 | Karasiuk | |
| 8,740,917 B2 | 6/2014 | Pilcher | |
| 8,814,836 B2 | 8/2014 | Ignon | |
| 8,945,104 B2 | 2/2015 | Boone, III | |
| 8,945,482 B2 | 2/2015 | Mitragotri | |
| 8,986,323 B2 | 3/2015 | Boone, III | |
| 9,044,582 B2 | 6/2015 | Chang | |
| 9,050,133 B1 | 6/2015 | Boone, III | |
| 9,056,193 B2 | 6/2015 | Ignon | |
| 9,085,795 B2 | 7/2015 | Day | |
| 9,186,490 B2 | 11/2015 | Chang | |
| 9,328,324 B2 | 5/2016 | Mitragotri | |
| 9,468,464 B2 | 10/2016 | Shadduck | |
| 9,474,886 B2 | 10/2016 | Ignon | |
| 9,486,615 B2 | 11/2016 | Ignon | |
| 9,492,686 B2 | 11/2016 | Da Silva | |
| 9,498,610 B2 | 11/2016 | Roger | |
| 9,517,085 B2 | 12/2016 | Karasiuk | |
| 9,550,052 B2 | 1/2017 | Ignon | |
| 9,566,088 B2 | 2/2017 | Ignon | |
| 9,642,997 B2 | 5/2017 | Ignon | |
| 9,655,432 B2 | 5/2017 | Boone, III | |
| 9,662,482 B2 | 5/2017 | Ignon | |
| 9,775,645 B2 | 10/2017 | Boone, III | |
| 9,775,646 B2 | 10/2017 | Shadduck | |
| 9,814,422 B2 | 11/2017 | Mitragotri | |
| 9,814,868 B2 | 11/2017 | Ignon | |
| 9,833,261 B2 | 12/2017 | Boone, III | |
| 9,848,853 B2 | 12/2017 | Mitragotri | |
| 9,909,098 B2 | 3/2018 | Mitragotri | |
| 9,918,727 B1 | 3/2018 | Boone, III | |
| 10,022,151 B2 | 7/2018 | Jansen | |
| 10,035,007 B2 | 7/2018 | Ignon | |
| 10,080,428 B2 | 9/2018 | Kern | |
| 10,130,390 B1 | 11/2018 | Hart | |
| 10,136,976 B2 | 11/2018 | Miyamichi | |
| 10,172,644 B2 | 1/2019 | Ignon | |
| 10,179,229 B2 | 1/2019 | Ignon | |
| 10,238,812 B2 | 3/2019 | Ignon | |
| 10,238,849 B2 | 3/2019 | Britva | |
| 10,251,675 B2 | 4/2019 | Ignon | |
| 10,252,044 B2 | 4/2019 | Bock | |
| 10,357,641 B2 | 7/2019 | Ignon | |
| 10,357,642 B2 | 7/2019 | Ignon | |
| 10,456,321 B2 | 10/2019 | Shadduck | |
| 10,485,983 B1 | 11/2019 | Boone, III | |
| 10,492,807 B1 | 12/2019 | Boone, III | |
| 10,524,835 B2 | 1/2020 | Shadduck | |
| 10,556,096 B2 | 2/2020 | Ignon | |
| 10,556,097 B2 | 2/2020 | Ignon | |
| 10,758,261 B2 | 9/2020 | Richardson | |
| 10,765,199 B2 | 9/2020 | Kern | |
| 10,772,473 B2 | 9/2020 | Johnstone | |
| 10,835,287 B2 | 11/2020 | Shadduck | |
| 10,898,227 B2 | 1/2021 | Boone, III | |
| 10,912,428 B2 | 2/2021 | Daffer | |
| 10,993,743 B2 | 5/2021 | Ignon | |
| 11,020,577 B2 | 6/2021 | Ignon | |
| 11,202,657 B2 | 12/2021 | Ignon | |
| 11,213,321 B2 | 1/2022 | Ignon | |
| 11,224,728 B2 | 1/2022 | Ignon | |
| 11,291,474 B2 | 4/2022 | Nicolas | |
| 11,446,477 B2 | 9/2022 | Ignon | |
| 11,517,350 B2 | 12/2022 | Ignon | |
| 2002/0016601 A1 | 2/2002 | Shadduck | |
| 2004/0122447 A1 | 6/2004 | Harmon | |
| 2004/0249320 A1 * | 12/2004 | Yamazaki | A61H 23/0263 |
| | | | 601/46 |
| 2006/0058714 A1 * | 3/2006 | Rhoades | A46B 5/0016 |
| | | | 601/72 |
| 2006/0253125 A1 | 11/2006 | Ignon | |
| 2007/0198031 A1 | 8/2007 | Kellogg | |
| 2009/0004953 A1 * | 1/2009 | Kinsey | A61B 17/54 |
| | | | 451/163 |
| 2009/0157094 A1 | 6/2009 | Yeshurun | |
| 2010/0045427 A1 | 2/2010 | Boone, III | |
| 2010/0049177 A1 * | 2/2010 | Boone, III | A61H 9/0057 |
| | | | 606/9 |
| 2010/0198119 A1 * | 8/2010 | Gubernick | A61B 17/54 |
| | | | 601/69 |
| 2011/0082415 A1 * | 4/2011 | Ignon | A61M 37/00 |
| | | | 604/22 |
| 2012/0330194 A1 | 12/2012 | Britva | |
| 2013/0110032 A1 * | 5/2013 | Luzon | A45D 34/041 |
| | | | 606/131 |
| 2013/0158547 A1 | 6/2013 | David | |
| 2014/0202493 A1 * | 7/2014 | Zelickson | B23Q 5/046 |
| | | | 134/6 |
| 2015/0045723 A1 | 2/2015 | Paithankar | |
| 2015/0088050 A1 * | 3/2015 | Chang | A61N 1/327 |
| | | | 604/20 |
| 2016/0045081 A1 * | 2/2016 | Kern | A46B 13/008 |
| | | | 15/22.4 |
| 2016/0128894 A1 | 5/2016 | Horton | |
| 2017/0036002 A1 | 2/2017 | Ignon | |
| 2017/0056636 A1 * | 3/2017 | Shadduck | A61H 9/0057 |
| 2017/0360464 A1 | 12/2017 | Jurna | |
| 2018/0110538 A1 | 4/2018 | Bailar | |
| 2018/0140329 A1 | 5/2018 | Beijens | |
| 2018/0235662 A1 | 8/2018 | Horton | |
| 2020/0015841 A1 * | 1/2020 | Friend | A61B 17/54 |

(56)　　　　　　References Cited

U.S. PATENT DOCUMENTS

| | | | |
|---|---|---|---|
| 2020/0085470 A1 | 3/2020 | Shadduck | |
| 2020/0222269 A1 | 7/2020 | Rodan | |
| 2020/0330270 A1 | 10/2020 | Foster | |
| 2020/0360044 A1 | 11/2020 | Bailar | |
| 2021/0186552 A1* | 6/2021 | Farrow | A61B 17/320068 |
| 2021/0204982 A1 | 7/2021 | Nicolas | |
| 2022/0117632 A1* | 4/2022 | Walker | A61B 17/54 |
| 2022/0362529 A1* | 11/2022 | Castro | A61N 1/403 |
| 2023/0329738 A1* | 10/2023 | Bigio Roitman | A61B 17/54 |

FOREIGN PATENT DOCUMENTS

| | | | |
|---|---|---|---|
| WO | 2021089162 A1 | 5/2021 |
| WO | 2023039524 A1 | 3/2023 |
| WO | 2023064718 A1 | 4/2023 |
| WO | 2024129774 A1 | 6/2024 |
| WO | 2024186444 A1 | 9/2024 |
| WO | 2024215935 A1 | 10/2024 |
| WO | 2024233567 A1 | 11/2024 |
| WO | 2025029827 A1 | 2/2025 |
| WO | 2025029949 A1 | 2/2025 |
| WO | 2025072509 A1 | 4/2025 |

OTHER PUBLICATIONS

Gio Pelle Skin Care, GP-PL-70 Installation, operation, and Maintenance Manual, 31 pp, Jan. 2014.
Samson Medical Technologies, Skinwave Brochure, 2 pp, Jun. 2019.

* cited by examiner

DEVICE AND METHOD FOR SKIN TREATMENT

CROSS-REFERENCE TO RELATED APPLICATIONS

This application claims priority to U.S. Provisional Application No. 63/362,921, filed on Apr. 13, 2022, incorporated herein by reference in its entirety.

FIELD OF THE INVENTION

The invention relates to the field of human skin treatment, more specifically to devices and methods for cleansing and care of a person's skin.

BACKGROUND OF THE INVENTION

Methods of dermabrasion, alternatively referred to as microdermabrasion, are among skin abrasion techniques known within the state of the art. Such methods may be performed for cleansing and subsequent care of a person's skin to improve the visual appearance of the patient. Some undesirable skin conditions that may be caused, for example, by acne, sun exposure, and aging processes may be treated.

The mechanical abrasion of the outer layer of epidermis of a patient's skin is performed by abrasive elements comprising abrasive surfaces or by free abrasive particles delivered to a patient's skin, for example in the flow of air. Sometimes methods are improved or strengthened by use of lowered pressure (vacuum), and/or a treatment liquid (serum).

The removal of small portions of the epidermis causes mild injury, followed by production of new skin cells, resulting in a new outer layer of skin. As a result, the skin looks smoother and rejuvenated.

Such therapies are normally delivered to the patient through handheld applicators equipped with a microdermabrasion tip. The applicator is typically connected to a main unit with a user interface. The main unit further typically includes treatment liquid containers, a lowered pressure source, and other components.

Methods typically comprise several consecutive steps, for example skin cleansing followed by subsequent care of a person's skin. The skin abrasion methods remove moisture from the skin, so the application of moisturizing creams or other similar hydration substances or compositions during the procedure is desirable.

The methods and devices according to the state of the art unfortunately have several disadvantages. One of the disadvantages of known methods and devices is significant skin irritation. The therapy is often painful and requires the use of local anesthetics.

Other disadvantages include low treatment efficacy, and/or risk of treatment liquid spillage during interruption and/or termination of the procedure. Additionally, the process is associated with waste production and tends to be messy.

A device which uses vibrations during the treatment has been disclosed within the state of the art, but unfortunately vibrations of the device are uncomfortable for therapy operators and cause hand pain and other hand inconveniences for the operator leading to imprecise treatment during the operation of such devices. Therefore, there is a need for a novel method and system for microdermabrasion which increases treatment efficacy while minimizing skin irritation, providing a safe and comfortable procedure for both the patient and operator providing the therapy.

BRIEF SUMMARY OF THE INVENTION

Abrasion methods for human skin treatment, as well as the devices for carrying out these methods, are provided. More specifically, devices and methods for cleansing and care of a person's skin, especially facial skin, are provided.

The device and methods effectively use a combination of mechanical abrasion strengthened by vibrations transmitted to an applicator tip, lowered pressure (vacuum) and treatment liquid (serum).

According to another aspect of the invention the following devices and methods are proposed including at least one of a removable or interchangeable applicator tip, bristled tip, lamellar tip or solid tip; vibrations transmitted to the whole applicator tip or to at least portion of the applicator tip, which may be formed by bristled tip, lamellar tip or solid tip; or dermabrasion device of specific treatment parameters according to the description below.

The methods and devices provide to the patient many benefits, including in particular cleaning the skin surface and pores including blackheads, reducing some skin imperfections like acne or sunspots, infusing nutrients and vitamins to the patient's skin in order to make the skin visually better, letting the patient leave with a refreshing feeling.

The methods may consist of at least three distinctive steps, namely exfoliation, extraction and protection.

One innovative aspect of the device is formed by an arrangement where vibrations are transmitted directly from a vibration mechanism to at least a portion of the applicator tip that is in contact with a patient's skin. The advantage of this aspect of the invention is that vibrations are targeted to the applicator tip as a whole, or to at least a portion of the applicator tip, which may be formed by a bristled tip, lamellar tip or solid tip. The vibration of the whole applicator is significantly lowered. Occurrences of hand pain and other inconveniences for the person providing the therapy are also reduced.

The other advantageous aspect of the device is a special design of the applicator for reducing the risk of spilling of serum during the end or during an interruption in the treatment.

DETAILED DESCRIPTION OF THE INVENTION

Figure 1:
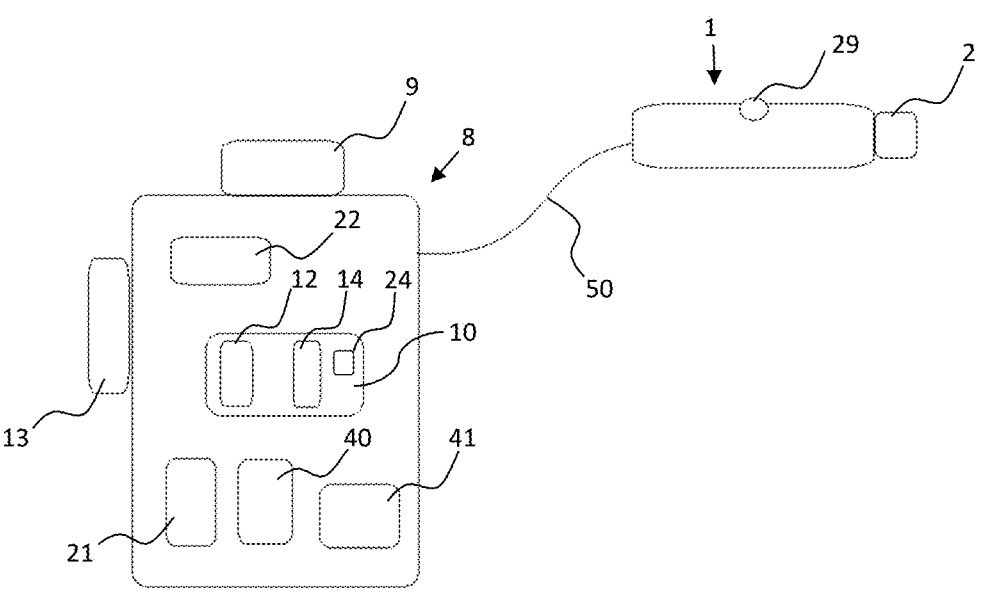
FIG. 1—A block diagram of a device according to the present invention

Abrasion methods for human skin treatment, as well as devices for carrying out these methods, are provided. More specifically, the devices and methods for cleansing and subsequent care of a person's skin, especially facial skin, are provided within present disclosure.

The methods may effectively use a combination of mechanical abrasion strengthened by vibrations, lowered pressure source and treatment liquid (serum).

Abrasion treatment methods may provide to the patient many benefits, including in particular cleaning the skin surface and pores including blackheads, reducing some skin imperfections like acne or sunspots, and infusing nutrients and vitamins to the patient's skin in order to make the skin better, letting the patient leave with a refreshing feeling.

The disclosed methods may consist of three distinctive steps, namely exfoliation, extraction and protection. Alternatively, additional steps may be added and the order of those steps may vary.

During the first step of exfoliation, the debris and dead cells are removed from the upper skin layers using at least one of the applicator tip with bristles, bristled tip or lamellar tip, treatment liquid (serum), lowered pressure, or a combination thereof. The heating/cooling of treatment liquid may be performed during this step. The appropriate temperature of the treatment liquid is mentioned below. The time range of the exfoliation step may be in the range of 30 seconds to 30 minutes, or in the range of 1 to 25 min, or in the range of 2 to 15 min, or in the range of 3 to 10 min.

In the following step of extraction, skin impurities are extracted using at least one of the applicator tip with bristles, bristled tip or lamellar tip, vibrations, treatment liquid, lowered pressure, or a combination thereof. The vibration movement of bristles may open the pores, so that the impurities may be extracted from them. Heating or cooling of the treatment liquid may take place during this step. The time range of the extraction step may be in the range of 30 seconds to 30 minutes, or in the range of 1 to 25 min, or in the range of 2 to 15 min, or in the range of 3 to 10 min.

In the last step of protection, protective substances, for example in the form of a cream, are applied to the patient's skin. The applicator tip equipped with a rugged surface or the solid tip may be used within this step for skin massage and enhancing absorption of protective substances to the skin. The vibrations may be used in this step. The time range of the protection step may be in the range of 30 seconds to 30 minutes, or in the range of 1 to 25 min, or in the range of 2 to 15 min, or in the range of 3 to 10 min.

Protective substances may be applied on the patient's skin before or instead of using the solid tip, for example with hands. Alternatively, protective substances may be applied as a part of the treatment liquid through the applicator tip 2.

Between the exfoliation and extraction steps, a peeling step may be included. A peeling mask may be applied, for example with hands. The time range of the peeling step may be in the range of 30 seconds to 30 minutes, or in the range of 1 to 25 min, or in the range of 2 to 15 min, or in the range of 3 to 10 min.

In addition to the disclosed methods, the device according to the invention has several benefits in comparison to the state of the art and brings some benefits to the patient.

One innovative aspect of the device is that vibrations are transmitted directly from the vibration mechanism via a transmission mechanism to the applicator tip as a whole or to at least a portion of the applicator tip that is in contact with the patient's skin.

A portion of the applicator tip that is in contact with patient's skin may be formed by at least one of: a rim, bristles, a bristled tip, a lamellar tip, a solid tip, or a portion of the applicator tip equipped with a rugged surface.

The advantage of this aspect of the invention is that vibrations are targeted to at least a portion of the applicator tip, while the vibration of the whole applicator is, in comparison with methods and devices within the state of the art, significantly lowered, and as a result the occurrence of hand pain and other inconveniences for the person providing the therapy is reduced.

Another advantageous aspect of the device is that the applicator is designed for reducing risk of spilling of treatment liquid when the treatment is stopped or interrupted.

A block diagram of the device according to the present invention is depicted in the FIG. 1. The device comprises the handheld applicator 1 with the applicator tip 2, which, during the therapy, comes into contact with patient's skin. The applicator tip 2, or at least a portion of the applicator tip 2, may be removable.

The applicator 1 is connected to the main unit 8 via connecting lumen 50, which may include at least one of: a communication cable, a cable for electric connection, a vacuum pipe 18, a treatment liquid pipe 19, or a combination thereof. The treatment liquid pipe 19 and vacuum pipe 18 serve to fluidly connect the applicator 1 and the main unit 8 and for inflow and outflow of fluids to/from the containers.

In one aspect of the invention, the applicator 1 may be equipped with an adjustable liquid inflow regulation 29. The volume of treatment liquid used during therapy may be in the range of 10 to 500 ml, or in the range of 50 to 100 ml, or in the range of 70 to 90 ml.

The main unit 8 may comprise a central control unit 22, a user interface 9, a lowered pressure source 21 and a power source 41. The lowered pressure source 21 may be in the form of a vacuum pump.

The user interface 9 may be formed by at least one of: a display, a touch screen, a keyboard, keypad, mouse, pointing device, or a combination thereof, or by any other appropriate user interface 9.

Some functions of the main unit 8 include, for example, switching the device on and off, displaying a value of lowered pressure, applying vibrations, flows of treatment liquid and rinsing fluid, opening and closing of containers, selecting from which container relevant liquids flow and so on. These functions may be controlled manually on the main unit by switches, buttons, control levers, regulation knobs, touchpads and the like.

The central control unit 22 may comprise a microprocessor and a memory with stored software, data, protocols, algorithms and the like for controlling the course of therapy.

The central control unit 22 may control and/or regulate a function of any part of the main unit 8 and/or the applicator 1.

For example, the central control unit 22 may control a switching system 24 for controlling the flow of fluids (treatment liquid and rinsing fluid) from the selected containers into the applicator 1.

The switching system 24 may comprise one or more pipes for fluid connection of the applicator 1 to the treatment liquid container 12 and/or the rinsing fluid container 14.

The switching system 24 may further comprise switching components for closing/opening the relevant pipes. The switching components may for example comprise one or more valves. The applicator 1 may be connected with treatment liquid container 12 and/or the rinsing fluid container 14 without using the switching elements.

The switching system 24 may be configured for selecting from which container, selected from a treatment liquid container 12 and a rinsing fluid container 14, relevant fluid should flow into the applicator 1. The flowing of fluids from container to the applicator 1 may be controlled mechanically, for example by valves or other switching components, or the switching components may be controlled manually on the main unit 8, or electronically via the user interface 9, or automatically by the preset programs stored in memory.

The main unit 8 may be further equipped with a container attachment 10 for connecting a treatment liquid container 12, a waste container 13 or optionally a rinsing fluid container 14.

The containers may be formed of bottles having a volume in the range of 50-1000 ml, or in the range of 100-300 ml, or in the range of 120-250 ml. The material from which the bottles are formed may be transparent and/or translucent, allowing a user to see the fluid level, color, or other parameters. The containers may be made of glass or plastic, for example high density polyethylene, polycarbonate, PET, or polysulfone.

The treatment liquid container 12, and/or other containers, for example the waste container 13 or the rinsing fluid container 14, may be connected to the main unit 8 using a screw-thread, a bayonet connection, or any other appropriate connection.

Figure 16:
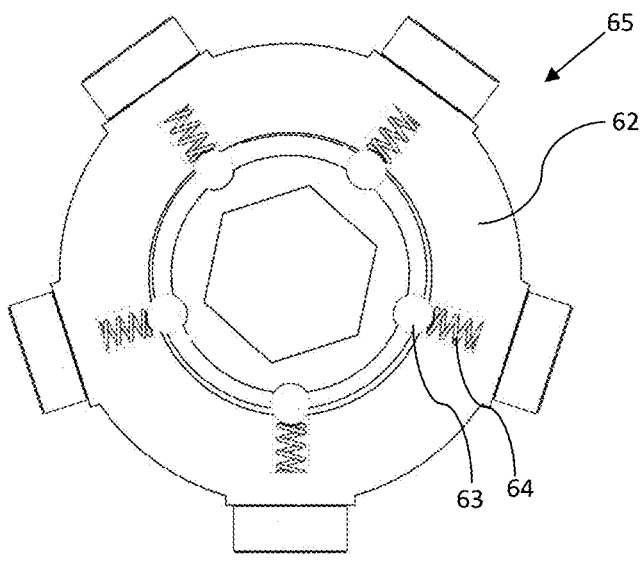

The treatment liquid container 12, and/or other containers, for example the waste container 13 or the rinsing fluid container 14, may be connected to the main unit 8 using a container fixing mechanism 65, which may comprise a fixing base 62, equipped with balls 63 on which the spring 64 exerts pressure, as depicted on FIG. 16. The ball 63 pushes on the part of the treatment liquid container 12, or other container, which is inserted into the fixing base 62. The treatment liquid container 12, or other container, which is inserted into the fixing base 62 may be equipped with a thread, collar, O-ring, or with any other appropriate part, which has a holding function and enables holding of the treatment liquid container 12, or other container, in the fixing base 62 with help of the balls 63. The treatment liquid container 12, or other container may be formed by a plastic bottle and may be equipped with a lid 61.

Figure 17:
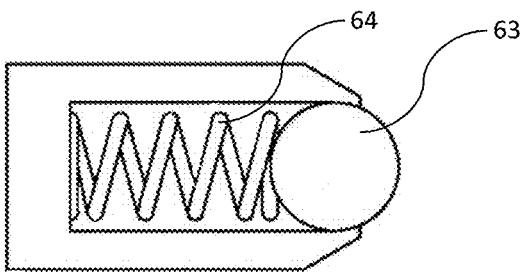

FIG. 17 shows a detail view of the container fixing mechanism 65 in the configuration where the spring 64 is pressing on the ball 63, which is in a position where it protrudes from the fixing base 62 to its internal hole and is prepared for fixing the container.

Figure 18:
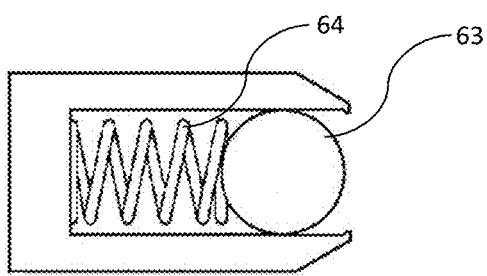

FIG. 18 shows a detail view of the container fixing mechanism in the configuration where the spring 64 is compressed due to the inserted container pressure (the container is not shown) on the ball 63, which is in a compressed position inside the fixing base 62 of the container fixing mechanism 65.

Figure 19:
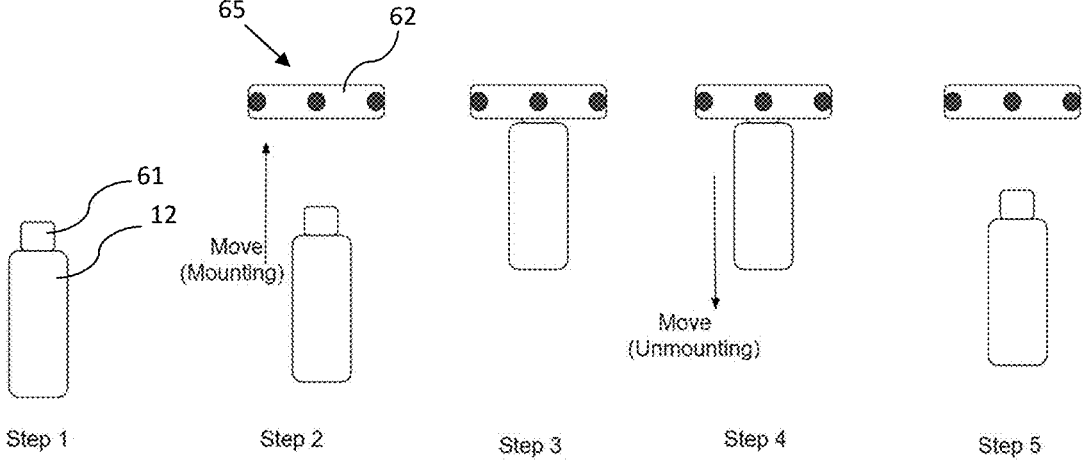

The scheme of inserting and removing the treatment liquid container 12 into the fixing base 62 is depicted in FIG. 19. The treatment liquid container 12 may be connected to the fixing base 62 by manual deployment using a certain pressure in the direction perpendicular to the plane of the fixing base 62.

The other container, for example the waste container 13 or the rinsing fluid container 14, may be connected to the main unit 8 in the same manner as the treatment liquid container 12 using the container fixing mechanism.

The main unit 8 may comprise a switching system 24 for selecting from which container, selected from a treatment liquid container 12 and a rinsing fluid container 14, relevant fluid should flow into the applicator 1.

The removed unwanted skin structures, blood and other waste material from the patient's skin is transferred from the applicator 1 to the waste container 13 through vacuum pipe 18. The waste container 13 may be connected to the lowered pressure source 21, for example formed by the vacuum pump.

Figure 2:
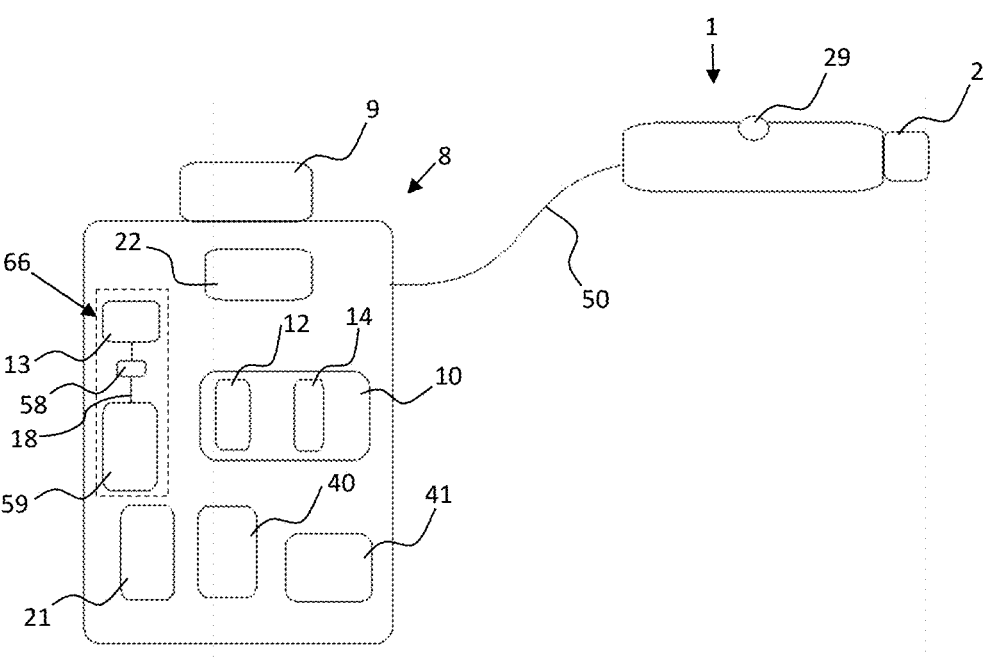
FIG. 2—A block diagram of a device according to the present invention with a waste management system FIG. 3—A handheld applicator according to the invention FIG. 4—A vibration mechanism of a handheld applicator according to present invention FIG. 5—A vibration mechanism of a handheld applicator with a shaft with tip base as one component FIG. 6—A removable bristled tip inserted into a tip base FIG. 7—A bristled tip FIG. 8—A bristled tip with individual bristles FIG. 9—A front view of the bristled tip with individual bristles FIG. 10—A lamellar tip FIG. 11—A front view of the lamellar tip FIG. 12—A solid tip with a hexagonal protrusion structure FIG. 13—A front view of the solid tip with hexagonal protrusion structure FIG. 14—A solid tip with protrusions in the shape of a part of a sphere FIG. 15—An arrangement of the applicator for reducing spilling of serum FIG. 16—A container fixing mechanism FIG. 17—A detail view of the container fixing mechanism when the spring is pressing on the ball, which is in a position where it protrudes from the container fixing mechanism FIG. 18—A detail view of the container fixing mechanism when the spring is compressed due to the inserted container pressure (the container is not shown) on the ball, which is in compressed position inside the container fixing mechanism FIG. 19—A diagram showing inserting and releasing of the container from the container fixing mechanism FIG. 20—A schematic diagram of the main components in the main unit—the main unit is shown divided into two parts FIG. 21—A schematic diagram of the main components in the main unit—the main unit is shown divided into two parts FIG. 22—A block diagram of a system for supplying electromagnetic energy through an applicator

The device according to the invention may contain a waste management system 66, which may comprise mainly the waste container 13, a valve 58 and a waste reservoir 59. The arrangement of the device according to the invention using the waste management system 66 is depicted on the FIG. 2. The waste container 13 may be connected through the vacuum pipe 18 with a valve 58 and with a waste reservoir 59, which may be adapted for easy waste disposal. The waste management system 66 may be equipped with sensors of the level of the waste fluid.

The waste container 13 may be emptied of waste material, for example at the end or during an interruption of the therapeutic procedure, by the opening of the valve 58. Waste material may be poured out to the waste reservoir 59. The waste management system 66, including the waste container 13, may be placed inside the main unit 8. The valve 58 and the sensors of the level of the waste fluid may be connected to the central control unit 22.

The waste container 13 may be formed by a bottle or any other appropriate container, the waste reservoir 59 may be formed by a bottle, or a drawer or a bathtub, that can be easily pulled out from the main unit 8, or may be formed by any other appropriate container.

The device may optionally be equipped with a heating/cooling system 40 for heating or cooling the treatment liquid or optionally for heating or cooling the rinsing fluid.

Figure 3:
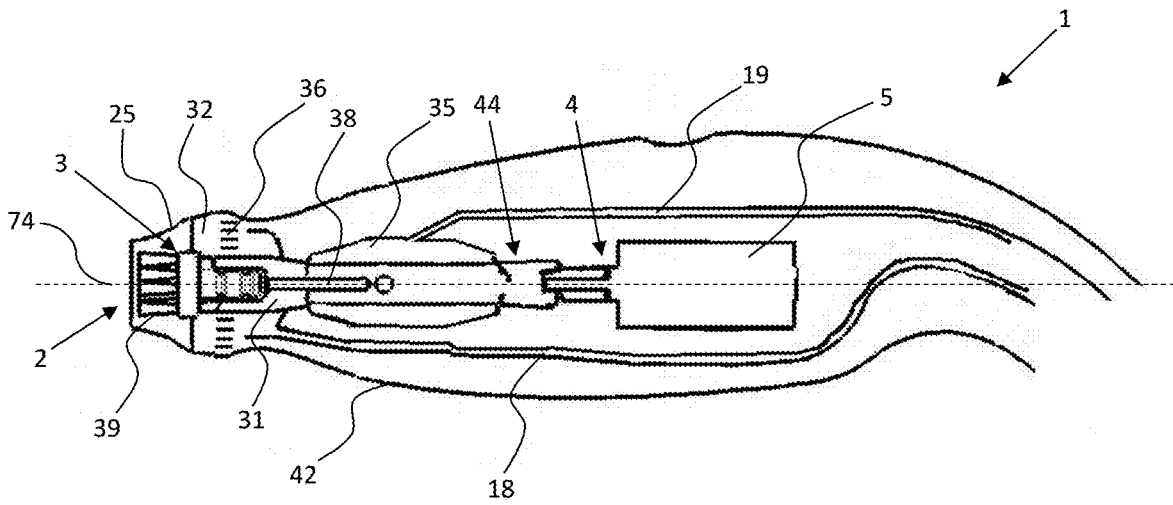

The device may be equipped with a handheld applicator 1 shown in FIG. 3. The applicator 1 is equipped with a vibration mechanism 4 and an applicator tip 2. The applicator tip 2 comes during the therapy into contact with the patient's skin. The vibrations are transmitted from the vibration mechanism 4 by transmission mechanism 44 to at least a portion of the applicator tip 2. In FIG. 3 is shown the longitudinal axis 74 of the applicator 1.

The applicator tip 2 may be removable. The applicator 1 is in fluid and electric communication with main unit 8. The treatment liquid pipe 19 and vacuum pipe 18 serve to fluidly connect the applicator 1 and the main unit 8 and for inflow and outflow of fluids to/from the containers.

The treatment liquid may be delivered to the patient's skin from the applicator tip 2 connected to a treatment liquid cavity 38 and a liquid inflow chamber 35 placed in the applicator 1, which is in fluid communication with treatment liquid container 12 via the treatment liquid pipe 19.

The applicator 1 may be equipped with a spilling reduction system 36, which forms a mechanical barrier preventing spilling of treatment liquid or rinsing fluid outside from the applicator 1.

The applicator 1 comprises applicator housing 42, in which the components of applicator 1 are positioned. The applicator housing 42 may be made of any appropriate material, for example plastic.

The applicator 1 in one aspect of the invention may have an ergonomic shape.

The vibration mechanism 4 may comprise electric rotary motor 5.

The applicator tip 2 in one aspect of the invention may be formed by the rim 25 and the bristled tip 3 equipped with bristles 39.

The applicator tip 2 in other aspects of the invention may be formed by at least one of: a bristled tip 3, bristles 39, a lamellar tip 68, a lamellar structure 67, a solid tip 52, a rim 25, a portion of the applicator tip 2 equipped with rugged surface, a rinsing tip, or a combination thereof.

The applicator tip 2 in one aspect of the invention may be made as one piece, for attachment to the applicator 1, and may be equipped with bristles 39 and/or with a rugged surface.

The applicator tip 2 in other aspects of the invention may comprise two separate portions, the rim 25 and a portion formed by the bristled tip 3 equipped with bristles 39 or by the solid tip 52 with a rugged surface. The bristled tip 3 may be interchangeable with the solid tip 52 by its placement on or in the applicator 1, for example to the tip base 31 situated in the applicator 1. The bristled tip 3 or the lamellar tip 68 or the solid tip 52 may be removable from the applicator 1 independently from the rest of the applicator tip 2, formed for example by the rim 25.

The applicator tip 2, in yet another aspect of the invention, may be formed by the rim 25 itself, wherein the bristles 39, the bristled tip 3, the lamellar tip 68, and the solid tip 52 are not applied.

The rim 25 may comprise a circular or elliptical shaped element. The rim 25 may be equipped with a sharp edge for effective skin abrasion. The rim 25 may be made of any appropriate material, for example the rim 25 may be made of plastic.

Figure 9:
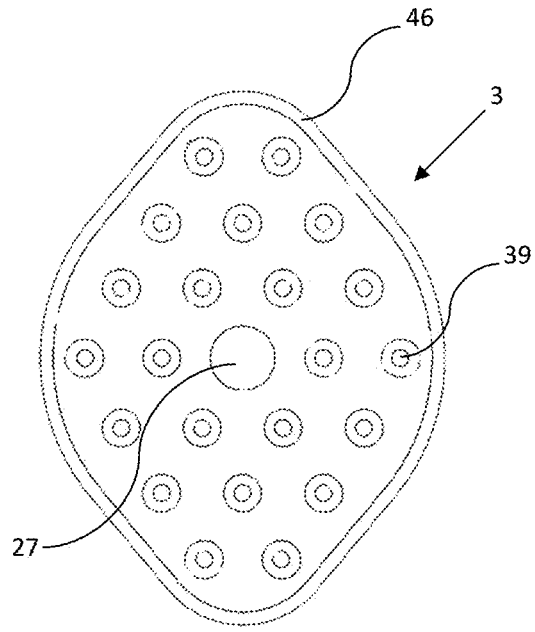
Figure 11:
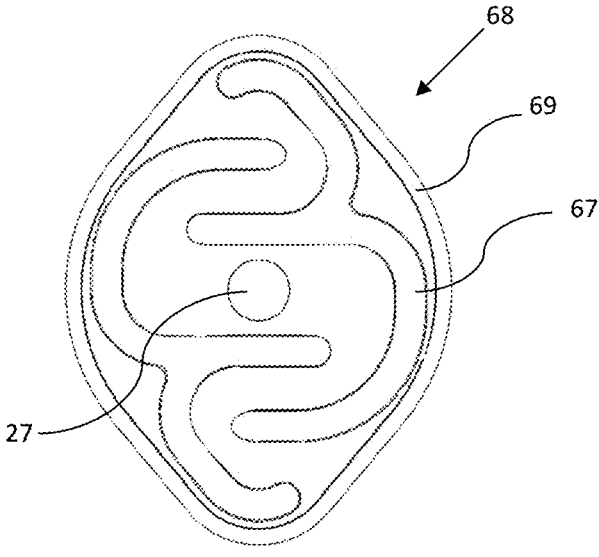

The applicator tip 2, or other part of the applicator 1, may comprise treatment liquid opening 27 and/or vacuum opening. The treatment liquid opening 27, shown for example in FIG. 9 and FIG. 11, provides flow of the treatment liquid from the treatment liquid pipe 19 to the patient's skin surface.

The vacuum opening provides suction for the waste treatment liquid, removing unwanted skin structures, blood, and other waste material to the vacuum pipe 18 and further to the waste container 13.

The treatment liquid opening 27 may be situated in a center of at least one of: applicator tip 2, the bristled tip 3, the lamellar tip 68, the solid tip 52, for example the treatment liquid opening 27 may be placed in the center of the pad 46 of the bristled tip or in the center of the pad 48 of the solid tip.

The bristles 39 may form a ring around treatment liquid opening 27 through which treatment liquid flows to the patient's skin.

The treatment liquid opening 27 may be also placed outside of the center of at least one of: the applicator tip 2, the bristled tip 3, the solid tip 52, for example the treatment liquid opening 27 may be placed in the applicator tip 2, outside of the center of applicator tip 2, or may be placed in the pad 46 of the bristled tip, outside of the center or the pad 46, or may be placed in the pad 48 of the solid tip, or outside of the center of the pad 48 of the solid tip. The treatment liquid opening 27 may be also placed in another part of the applicator 1, for example in the applicator base 32.

The placement of the treatment liquid opening 27 close to the patient's skin is advantageous for effective supply of the treatment liquid to the patient's skin.

The vacuum opening may be placed in the center of at least one of: the applicator tip 2, the bristled tip 3, the solid tip, for example the vacuum opening may be placed in the center of the pad 46 of the bristled tip, or in the center of the pad 48 of the solid tip.

The vacuum opening may be placed in the applicator tip 2, outside of the center of applicator tip 2, or may be placed in the pad 46 of the bristled tip, outside of the center of the pad 46 of the bristled tip, or may be placed in the pad 48 of the solid tip, or outside of the center of the pad 48 of the solid tip. The treatment liquid opening 27 may also be placed in another part of the applicator 1, for example in the applicator base 32.

The placement of the vacuum opening close to the patient's skin is advantageous for effective suction of the waste treatment liquid, the removed skin structures and other waste material from the applicator tip 2.

The applicator tip 2 is adapted for attachment to the applicator 1, for example by a threaded connection. The applicator tip 2 may be attached to the applicator base 32.

Figure 4:
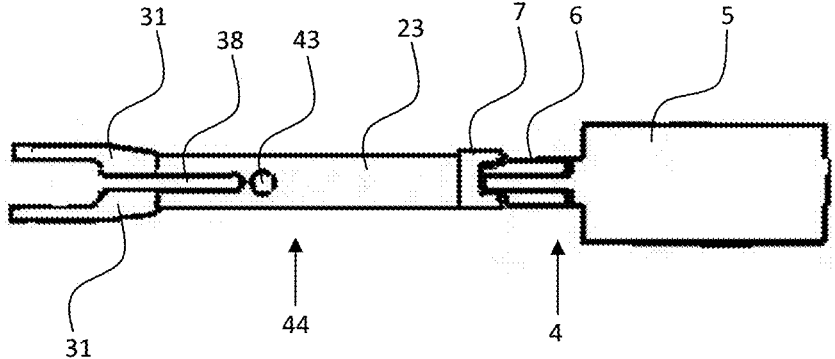

The vibration mechanism 4 of handheld applicator 1 according to the present invention is depicted in FIG. 4.

In one aspect of the invention, vibrations may be transmitted from the vibration source, formed by vibration mechanism 4, to at least a portion of the applicator tip 2 by a transmission mechanism 44, which is mechanically connected to a vibration source and to at least a portion of the applicator tip 2. The portion of the applicator tip 2, where vibrations may be transmitted to the patient, may be formed by at least one of: rim 25, bristles 39, bristled tip 3, solid tip 52, a portion of the applicator tip 2 with a rugged surface, or a combination thereof. For example, the portion of the applicator tip 2, where vibrations may be transmitted to the patient, may be formed by bristled tip 3 or solid tip 52.

The vibration source may comprise a vibration mechanism 4, placed in handheld applicator 1. The vibration mechanism 4 may comprise electric rotary motor 5, connected with eccentric element 6 and a shaft bed 7 for conversion of rotational motion to linear movement (for example vibration) in a direction perpendicular or substantially perpendicular to the longitudinal axis 74 of the applicator 1. The linear vibrations are further transmitted to the tip base 31 by the transmission mechanism 44 comprising a shaft 23 and a fixing pin 43. The shaft 23, through the tip base 31, further pass on the linear movement to at least a portion of the applicator tip 2, which may comprise for example the bristled tip 3 or the solid tip 52, which are to be placed into the tip base 31. The shaft 23 and the tip base 31 may comprise the treatment liquid cavity 38.

Figure 5:
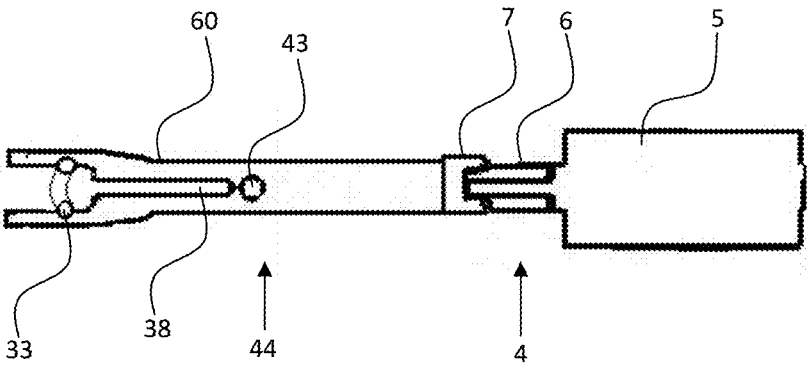

The tip base 31 and a shaft 23 may be made as one component forming the shaft 60 with tip base, as depicted on FIG. 5.

The tip base 31 may be equipped with an O-ring in order to facilitate placement of the applicator tip 2 into the tip base 31.

Figure 6:
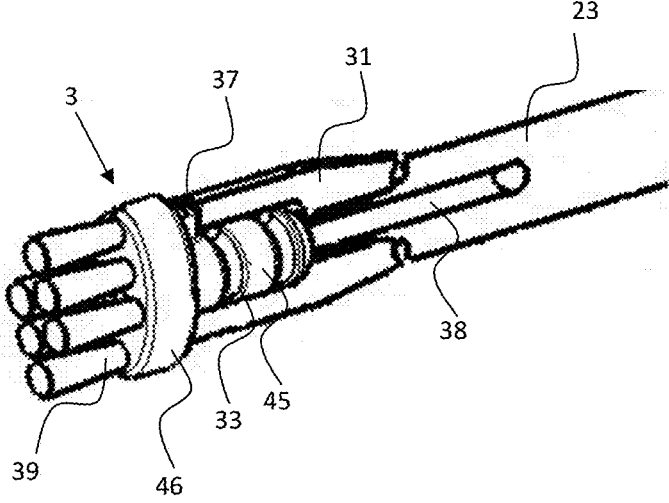

The bristled tip 3 may be placed in the tip base 31, as depicted on FIG. 3 and FIG. 6 and mentioned above.

The bristled tip 3 may be placed in the tip base 31 tightly, with no free space between the tip base 31 and the pad 46 of the bristled tip, or there may be distance between the tip base 31 and the pad 46 of the bristled tip, which may be in the range of 0.5 to 10 mm or in the range of 1 to 7 mm, or in the range of 2 to 5 mm.

In devices where the tip base 31 and shaft 23 are made as one component forming the shaft 60 with tip base, as depicted in FIG. 5, the bristled tip 3 may be placed into the shaft 60 with tip base with no free space between the shaft 60 with tip base and the pad 46 of the bristled tip, or there may be a distance between the shaft 60 with tip base and the pad 46 of the bristled tip, which may be in the range of 0.5 to 10 mm or in the range of 1 to 7 mm, or in the range of 2 to 5 mm.

Other tips, for example the solid tip 52 or the lamellar tip 68, may be used instead of the bristled tip 3 and may be placed in or on the tip base 31 or in or on the shaft 60 with tip base. There may be no free space between tip base 31 or the shaft 60 with tip base and the pad 48 of the solid tip or the pad 69 of the lamellar tip, or there may be a distance in the range of 0.5 to 10 mm, or in the range of 1 to 7 mm, or in the range of 2 to 5 mm. The arrangement with distance makes a more flexible structure than the arrangement without distance and facilitates vibrational movement and its transmission from the vibration mechanism 4 and transmission mechanism 44 to the patient's skin.

The electric rotary motor 5 may comprise a mini motor with a supply voltage in the range of 2.1V to 24V and with a speed in the range of 1500 to 60 000 rpm, or in the range of 5000 to 12 000 rpm. The term "mini motor" may be defined as the motor 5 has such dimensions that it is possible to be placed in the applicator 1.

The electric rotary motor 5 may be firmly placed in the applicator 1, for example by placement into a motor bed surrounding the electric rotary motor 5. The motor bed may be made for example from plastic, or from other appropriate materials.

It is advantageous for reducing vibrations of the applicator 1, to place a vibration reducing element between the applicator housing 42 and at least one of the electric rotary motor 5, the vibration mechanism 4, the transmission mechanism 44, the eccentric element 6, the shaft bed 7, the shaft 23, the tip base 31, or a combination thereof.

The vibration reducing element may be made for example from rubber, silicone or from other appropriate materials.

The linear motion of the shaft 23 transmitted to the applicator tip 2 as a whole, or to at least a portion of the applicator tip 2, which is in contact with a patient's skin, which may be formed for example by the bristled tip 3 or the solid tip 52, takes place in a direction perpendicular, or substantially perpendicular, to the longitudinal axis 74 of the applicator 1 and/or in a direction perpendicular, or substantially perpendicular, to the longitudinal axis of the shaft 23.

As mentioned above, the applicator tip 2 as a whole, the bristled tip 3, or other relevant portion of the applicator tip 2, for example the solid tip 52, performs linear motion.

In the context of the present disclosure, it is understood that in some embodiments "linear motion" may encompass pure linear motion but also substantially or primarily linear motion, for example motion of at least a portion of the applicator tip 2 which may comprise bristled tip 3 or solid tip 52 formed by rotational motion of the applicator tip about an axis, for example an axis defined by fixing pin 43, wherein the radius of rotation is sufficiently long, and the arc length of rotation is sufficiently short in relation to the radius, that the motion of the applicator tip 2 is substantially or primarily linear.

The motion of the applicator tip 2 as a whole, or the motion of the portion of the applicator tip 2 may be linear, as mentioned above. The construction of the vibration mechanism 4 and transmission mechanism 44 is not limited to the construction described above and resulting motion of the applicator tip 2 as the whole, or the motion of the portion of the applicator tip 2 may be for example at least one of: linear horizontal, linear vertical, linear in another direction, circular, partially circular in limited angle to one side and then back to the other, triangular, square, pentagonal, hexagonal, heptagonal, octagonal, or a combination thereof, or any other appropriate motion. The described motion is considered from the front view from the position against the applicator tip 2. All these types of motion of the applicator tip 2 as a whole, or the motion of at least a portion of the applicator tip 2 may take place in a direction perpendicular, or substantially perpendicular, to the longitudinal axis 74 of the applicator 1 and/or in a direction perpendicular, or substantially perpendicular to the longitudinal axis of the shaft 23.

In an alternative embodiment of the invention, the motion of the applicator tip 2 as a whole, or the motion of the portion of the applicator tip 2 may take place in a parallel direction to the longitudinal axis 74 of the applicator 1.

The range of motion of the applicator tip 2 as a whole, or the motion of the portion of the applicator tip 2, comprising for example bristled tip 3, may be influenced by the length of the shaft 23, and/or the position of the fixing pin 43 in the shaft 23. For example the length of the part of the shaft 23 between the center of the fixing pin 43 and end of the shaft 23 connected to the tip base 31 may be in the range of 5 mm to 200 mm, or in the range of 8 to 100 mm, or in the range of 10 to 30 mm, and the length of the part of the shaft 23 between the center of the fixing pin 43 and the end of shaft 23 connected to the eccentric element 6 may be in the range of 5 mm to 200 mm, or in the range of 8 to 100 mm, or in the range of 15 to 50 mm.

The range of motion of the applicator tip 2 may be further influenced by the angle of motion around the axis, for example as formed by the shaft 23 and fixing pin 43. In various embodiments, the angle of motion may be in the range of 0.01 degrees to 20 degrees, or 1 degree to 10 degrees, or 1 degree to 5 degrees, or 2 degrees to 3 degrees, or any other suitable angle.

The vibration frequency, or in other words a frequency of the linear movement, may be defined as the number of movements between the edge positions of the end of the shaft 23 on the side opposite to the side of the electric motor 5 placement, wherein the linear movement of the end of the shaft 23 takes place in the direction perpendicular, or substantially perpendicular, to the longitudinal axis of the shaft 23. The ratio between the vibration frequency and the number of rotations of the electric motor 5 may be 1:2, as it is in the exemplary aspect of the invention depicted in FIG. 4. The ratio between the vibration frequency and the number of rotations of the electric motor 5 may be any other appropriate ratio, based on the construction of the vibration mechanism 4 and transmission mechanism 44. For example, the ratio between the vibration frequency and the number of rotations of the electric motor 5 may be 1:3 or 1:4, or 1:5 or 1:6 or 1:7 or 1:8, or any other appropriate ratio.

The vibration frequency may be adjustable on the user interface 9 of the main unit 8 or may be regulated manually on the main unit 8. The vibration frequency may be in the range of 1 000 to 100 000 moves per minute, or in the range of 1 500 to 90 000 moves per minute, or in the range of 3 000 to 120 000 moves per minute, or in the range of 5 000 to 80 000 moves per minute, or in the range of 5 000 to 24 000 moves per minute, or in the range of 30 000-40 000 moves per minute.

In one aspect of the invention, a treatment liquid is delivered to the patient's skin from treatment liquid opening 27 in the applicator 1 connected to a treatment liquid cavity 38 and a liquid inflow chamber 35, which is in fluid communication with treatment liquid container 12 via the treatment liquid pipe 19.

The inserting of removable bristled tip 3 into the handheld applicator 1 is depicted in FIG. 6.

In one aspect of the invention, the bristled tip 3 may be removable from the applicator 1 and may be placed in the tip base 31, which is connected to the shaft 23.

The shaft 23 and the tip base 31 may comprise the treatment liquid cavity 38 for treatment liquid inflow to the applicator tip 2.

The bristled tip 3 may be removable from the applicator 1 independently of the rest of the applicator tip 2, for example independently of the rim 25. The removable bristled tip 3 may be interchangeable with the solid tip 52 by its placement into the tip base 31.

As mentioned above, the applicator tip 2, according to another aspect of the invention, may be made as one piece equipped with fixed bristles 39. The bristles 39 in this aspect of the invention may be attached to and/or removed from the applicator 1 as a portion of the entire applicator tip 2.

The vibrations are transmitted from the vibration mechanism 4 by transmission mechanism 44 to at least a portion of the applicator tip 2. In this case, the applicator tip 2 is equipped with bristles 39 and/or the applicator tip 2 comprises the bristled tip 3 with bristles 39, the ends of bristles 39 perform a linear movement in a direction perpendicular, or substantially perpendicular, to the longitudinal axis of the shaft 23. The ends of bristles 39 perform the linear movement in the length between edge positions of the movement of bristles 39. The length between edge positions of the movement of bristles 39 may be in the range of 0.01 to 10 mm, or in the range of 0.1 to 5 mm, or in the range of 1 to 2 mm, or in the range of 1.4 to 1.8 mm.

Figure 7:
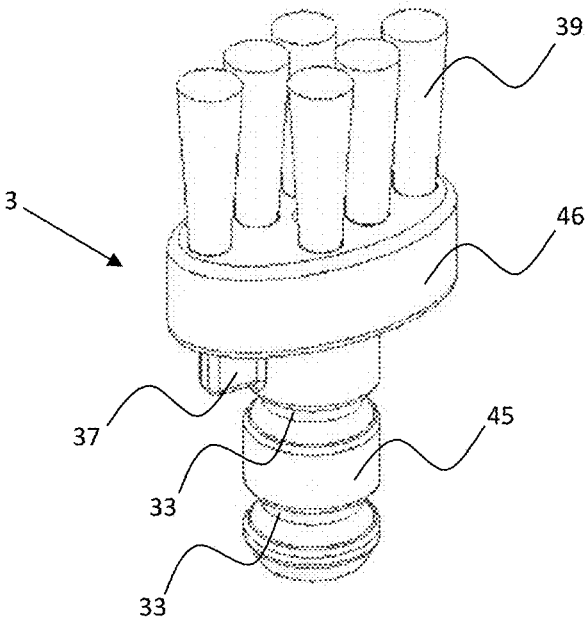

One embodiment of the bristled tip 3 is depicted in FIG. 7.

The applicator tip 2, according to one aspect of the invention, may comprise bristled tip 3 as a separate portion of the applicator tip 2. The bristled tip 3 may be removable from the applicator 1, independently of the rest of the applicator tip 2, formed for example by the rim 25, if applied. The bristled tip 3 may be placed in the tip base 31 in the applicator 1. The bristled tip 3 may be placed in the applicator 1 without other parts of the applicator tip 2.

The bristled tip 3 may comprise a stalk 45 of the bristled tip and a pad 46 of the bristled tip equipped with bristles 39. The stalk 45 of the bristled tip may comprise at least one o-ring 33 to stabilize the location of the stalk 45 of the bristled tip, when it is placed in the tip base 31 in the applicator 1. In order to prevent rotational movement of the bristled tip 3 when it is placed in the tip base 31, the bristled tip 52 may be secured by a fixing position pin 37, placed on the stalk 45 of the bristled tip. This is advantageous mostly in cases where the pad 46 of the bristled tip has an elliptical shape.

In other aspects of the invention, the whole applicator tip 2 comprising the bristles 39 may be removable from the applicator 1. In yet another aspect of the invention, the bristled tip 3 may be removable from the applicator tip 2 independently of the rest of the applicator tip 2, which may be formed for example by the rim 25.

The length of bristles 39 used in the applicator tip 2 or in the bristled tip 3 may be in the range of 2 to 25 mm, or in the range of 4 to 15 mm, or in the range of 5 to 10 mm, or in the range of 6 to 9 mm. The offset of the bristles 39 from the rim 25 of the applicator tip 2 may be in the range of 0 to 8 mm, or in the range of 0 to 4 mm, or in the range of 0 to 2 mm. The bristles 39 may be placed in the applicator tip 2 without offset from the rim 25. The edges of bristles 39 may also be situated in the applicator tip 2 above the rim 25, wherein the bristles 39 protrude from the rim 25.

In one aspect of the invention, the group of bristles 39, placed in the applicator tip 2 or in the bristled tip 3, may have a circular cross-section. The diameter of the group of bristles 39 may be in the range of 0.5 to 20 mm, or in the range of 3 to 15 mm, or in the range of 5 to 12 mm. The term "diameter" is used to refer to the diameter of a circle that describes the largest cross section of the group of bristles 39.

Each individual bristle 39 may have a diameter in the range of 0.05 to 2 mm, or in the range of 0.08 to 1 mm, or in the range of 0.1 to 0.5 mm.

The applicator tip 2 or bristled tip 3 may comprise tufts of bristles 39 with diameters in the range of 0.1 to 15 mm, or in the range of 2.5 to 12 mm, or in the range of 5 to 10 mm. The number of tufts of bristles 39 may be in the range of 1 to 100, or in the range of 2 to 40, or in the range of 5 to 30, or in the range of 7 to 15.

The total number of bristles 39 in the applicator tip 2 or bristled tip 3 may be in the range of 4 to 1000, or in the range of 25 to 500, or in the range of 35 to 145.

The bristles 39 may have a stiffness grade in the range of 0.5 to 30 centinewtons per square millimeter, or in the range of 1 to 25 centinewtons per square millimeter, or in the range of 5 to 20 centinewtons per square millimeter, or in the range of 10 to 15 centinewtons per square millimeter.

The bristles 39 may be made from any synthetic or natural materials, or from a combination thereof. The synthetic materials may be selected from a group of polymers, for example polyethylenes, polyamides, e.g. nylon, polyethylene terephthalate, polybutylene terephthalate, resins, polyesters, halogenated polymers, polyacrylates, polysulfones, and other appropriate materials, or their combinations. The natural materials for bristles 39 may be selected from a group of: cellulose fibers, cotton fibers, hair of a boar, cow, horse or goat, and other appropriate materials, or their combinations. The natural materials may be biodegradable.

The bristles 39 may be attached to the applicator tip 2 or the bristled tip 3, for example, by melting, gluing, stapling, or by other appropriate attachment methods, or by a combination thereof.

The applicator tip 2, according to one aspect of the invention, may comprise bristled tip 3 as a separate portion of the applicator tip 2. The bristled tip 3 may be in the form as depicted in FIG. 7 and may comprise a group of individual bristles 39 or may comprise a group of bristles divided into tufts of individual bristles 39.

Figure 8:
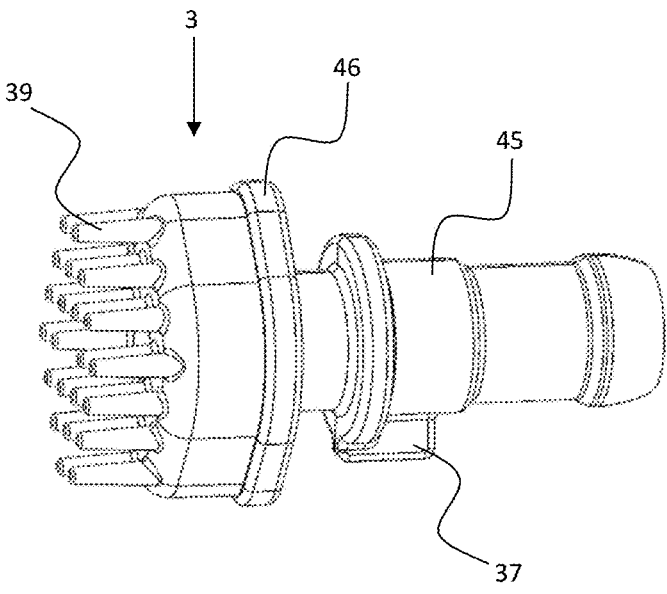

The bristled tip 3 may comprise a group of individual bristles 39 with a larger diameter, as depicted in FIG. 8 and in its front view in FIG. 9. The diameter of individual bristles 39 may be in the range of 0.2 to 5 mm, or in the range of 0.3 to 3 mm, or in the range of 0.5 to 2 mm.

The length of bristles 39 may be in the range of 0.3 to 15 mm, or in the range of 1 to 10 mm, or in the range of 2 to 8 mm. The bristles 39 in this form of the bristled tip 3 may be made for example from silicone or rubber, for example nitrile butadiene rubber (NBR), ethylene propylene rubber (EPDM), fluorine rubber (FKM), or thermoplastic rubber (TPR). The hardness of bristles 39 in this form of the bristled tip 3 may be in the range of 40 to 95 Shore A, or in the range of 50 to 85 Shore A, or in the range of 60 to 80 Shore A.

The pad 46 of the bristled tip may have an elliptical shape with a length of a major axis in the range of 5 to 35 mm, or in the range of 7 to 20 mm, or in the range of 10 to 15 mm and length of a minor axis in the range of 5 to 35 mm, or in the range of 7 to 20 mm, or in the range of 10 to 15 mm.

The pad 46 of the bristled tip may be also have a circular shape with a diameter in the range of 5 to 35 mm, or in the range of 7 to 20 mm, or in the range of 10 to 15 mm.

The height of the pad 46 of the bristled tip may be in the range of 1 to 15 mm, or in the range of 2 to 12 mm, or in the rage of 3 to 10 mm, or in the range of 4 to 6 mm.

The length of the stalk 45 of the bristled tip may be in the range of 5 to 35 mm or in the range of 7 to 20 mm, or in the range of 8 to 15 mm, or in the range of 10 to 12 mm. The diameter of the stalk 45 of the bristled tip may be in the range of 1 to 12 mm, or in the range of 2 to 10 mm, or in the range of 3 to 6 mm.

The stalk 45 of the bristled tip may be made from any appropriate material, for example from plastic, polysulfone and/or many other polymers may be used. Other appropriate materials include, but are not limited to, wood, bamboo, rubber, or silicone.

The pad 46 of the bristled tip may be made from a similar material as the stalk 45 of the bristled tip, for example from a polymer material. The metal material can also be used for the pad 46 of the bristled tip.

Figure 14:
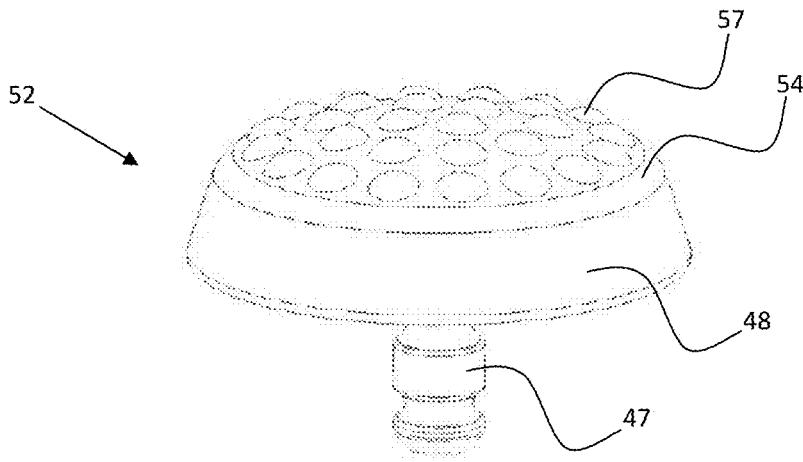

The solid tip 52 according to present invention is depicted in FIG. 14.

In one aspect of the invention the applicator tip 2 may comprise a solid tip 52, which may be used for skin massage and/or enhancement of absorption of protective substances into the patient's skin. The solid tip 52 may be equipped with a rugged surface. The solid tip 52 may be removable from the applicator 1 independently of the rim 25, if applied. The solid tip 52 may be placed in the applicator 1 without other parts of the applicator tip 2.

The solid tip 52 may comprise a stalk 47 of the solid tip and a pad 48 of the solid tip. The solid tip 52 may comprise the rugged surface pad 54.

The rugged surface may contain abrasive particles and/or may be uneven, rough, ragged, contoured, grooved, embossed, channeled, textured and/or may be formed by other type of surface facilitating dermabrasion and/or skin massaging functions.

The rugged surface pad 54 may be made with protrusions 57 in any appropriate shape. The rugged surface pad 54 may be made with protrusions 57 having a shape of at least one of rounded, spherical, circular, elliptical, linear, square, rectangular, curved, or a combination thereof. For example the rugged surface pad 54 may be made with protrusions 57 in the shape of a part of a sphere, as shown in the FIG. 14, and/or with protrusions 57 formed by ribs.

The rugged surface pad 54 may be made for example of silicone, rubber, plastic and/or of other appropriate material.

The hardness of the rugged surface pad 54 may be in the range of 10 to 100 Shore A, or in the range of 20 to 90 Shore A, or in the range of 50 to 90 Shore A.

The stalk 47 of the solid tip may comprise at least one O-ring 33 to stabilize the location of the stalk 47 of the solid tip, when it is placed in the tip base 31 in the applicator 1. The stalk 47 of the solid tip, when it is placed in the tip base 31, may be secured by a fixing position pin 37 of the solid tip, placed on the stalk 47 of the solid tip, for example in order to prevent rotational movement of the stalk 47.

The length of the stalk 47 of the solid tip may be in the range of 5 to 35 mm, or in the range of 7 to 20 mm, or in the range of 8 to 15 mm, or in the range of 10 to 12 mm. The diameter of the stalk 47 of the solid tip may be in the range of 1 to 12 mm, or in the range of 2 to 10 mm, or in the range of 3 to 6 mm.

The pad 48 of the solid tip may have an elliptical shape. The length of major axis of the pad 48 of the solid tip may be in the range of 5 to 35 mm, or in the range of 7 to 20 mm, or in the range of 10 to 15 mm. The length of minor axis of the pad 48 of the solid tip may be in the range of 5 to 35 mm, or in the range of 7 to 20 mm, or in the range of 10 to 15 mm.

The pad 48 of the solid tip may have a circular shape with a diameter in the range of 5 to 35 mm, or in the range of 7 to 20 mm, or in the range of 10 to 15 mm. The height of the pad 48 of the solid tip may be in the range of 1 to 15 mm, or in the range of 2 to 12 mm, or in the rage of 3 to 10 mm, or in the range of 4 to 6 mm.

The stalk 47 of the solid tip may be made from any appropriate material, for example from plastic. Polysulfones and/or many other polymers may be used for the stalk 47 of the solid tip. Other appropriate materials include, but are not limited to, wood, bamboo, rubber, or silicone.

The pad 48 of the solid tip may be made for example from a polymer material. A metal material can also be used for the pad 48 of the solid tip.

The applicator tip 2 and/or the solid tip 52 may comprise a hard material for enhancing the removal of unwanted skin structures. The applicator tip 2 and/or the solid tip 52 may comprise an abrasive material, for example in the form of abrasive particles fixed to a suitable carrier. The abrasive material may comprise at least one of diamond, corundum, aluminum oxide, or a combination thereof, and/or other abrasive materials. The hard material may be formed for example by hard plastic. The hard and/or abrasive material may be placed in at least one of the applicator tip 2, the solid tip 52, the rim 25, or a combination thereof.

Figure 12:
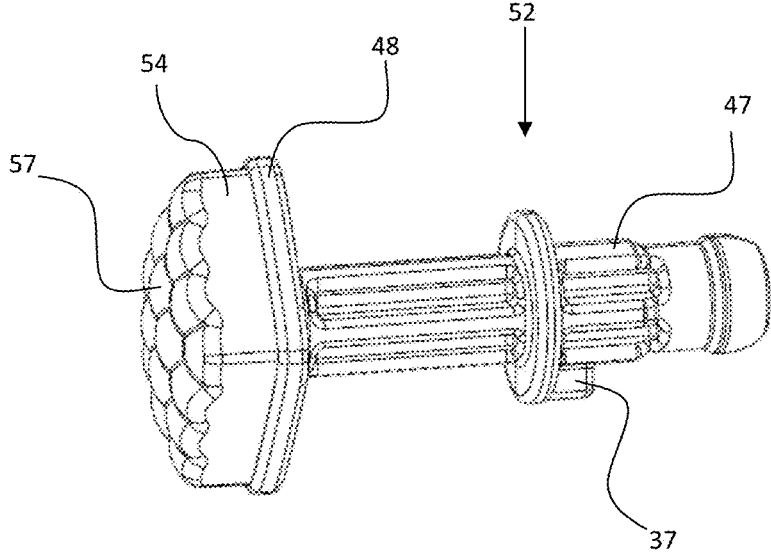
Figure 13:
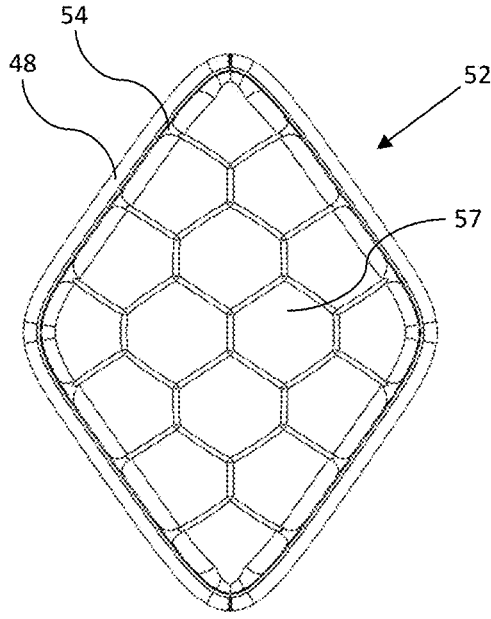

The solid tip 52 is depicted on FIGS. 12, 13 and 14.

The solid tip 52 may be made with protrusions 57 in the shape of a part of a sphere, as shown in FIG. 14.

The rugged surface pad 54 of the solid tip 52 may be made in a rounded diamond shape and equipped with a hexagonal protrusion structure as depicted in FIG. 12 and FIG. 13. FIG. 12 depicts the whole solid tip 52, which is equipped with the stalk 47 of the solid tip with fixing position pin 37, with pad 48 of the solid tip and also with the rugged surface pad 54 in the rounded diamond shape with hexagonal protrusions 57. FIG. 13 shows a front view to the solid tip 52 with the pad 48 of the solid tip with the rugged surface pad 54 both in rounded diamond shape with protrusions 57 in a hexagonal shape. The rugged surface pad 54 with protrusions 57 may be made for example from silicone or rubber, for example nitrile butadiene rubber (NBR), ethylene propylene rubber (EPDM), fluorine rubber (FKM), thermoplastic rubber (TPR).

The hardness of the protrusions 57 in the hexagonal shape may be in the range of 40 to 95 Shore A, or in the range of 50 to 85 Shore A, or in the range of 60 to 80 Shore A.

Figure 10:
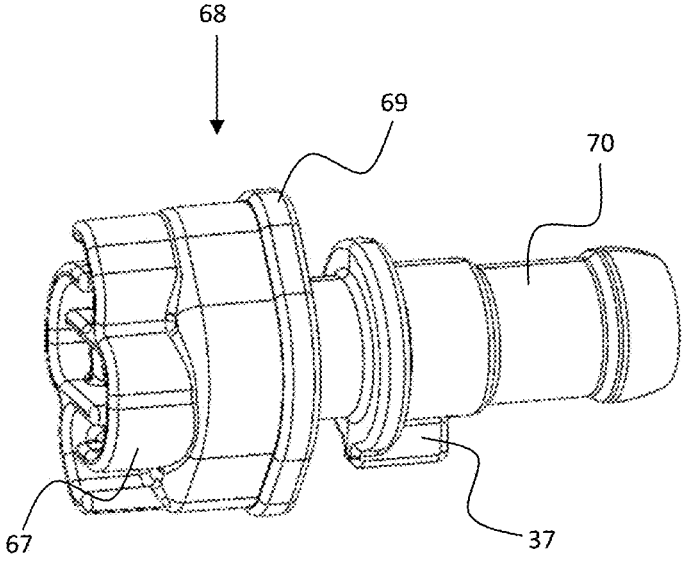

The applicator tip 2, according to one aspect of the invention, may comprise a lamellar tip 68 as a separate portion of the applicator tip 2, as depicted in FIG. 10 and FIG. 11. The lamellar tip 68 enables effective abrasion and cleansing of the patient's skin. The lamellar tip 68 may comprise a stalk 70 of the lamellar tip and a pad 69 of the lamellar tip with the lamellar structure 67.

The applicator tip 2 may be made as one component with the rim 25 and with the lamellar structure 67.

The lamellar structure 67 enables effective abrasion and cleansing the patient's skin. The lamellas ensure effective friction against the surface of the patient's skin and thus more effective cleansing of the skin. The lamellas may have a curved shape and an open structure, which is more advantageous, for example when compared to a closed structure of the grid with right angles, which makes it easier to drain the lamellar structure 67 of the treatment liquid, which may get away more easily. Generally, the structure in the form of a grid with right angles of lamellas, or another type of components with abrading and cleansing function, is not advantageous, because such a structure would not allow free movement of the treatment liquid.

The shape of the lamellas may be for example the shape as depicted in FIG. 10 and FIG. 11, or the shape of the letter "S" or any other appropriate curved shape. The lamellar structure 67 may be opened for better drainage of the treatment liquid.

The length of lamellas may be in the range of 0.2 mm to 50 mm, or in the range of 0.5 to 30 mm, or in the range of 1 to 20 mm.

The width of lamellas may be in the range of 0.2 mm to 4 mm, or in the range of 0.3 to 3 mm, or in the range of 0.5 to 2 mm.

The height of lamellas may be in the range of 0.3 to 15 mm, or in the range of 1 to 10 mm, or in the range of 2 to 8 mm.

The radius of the arc of curvature of the lamellar structure 67 may be in the range of 2 to 35 mm, or in the range of 4 to 25 mm, or in the range of 5 to 15 mm.

The lamellar structure 67 may be made for example from silicone or rubber, for example nitrile butadiene rubber (NBR), ethylene propylene rubber (EPDM), fluorine rubber (FKM), thermoplastic rubber (TPR).

The hardness of the lamellar structure 67 may be in the range of 40 to 95 Shore A, or in the range of 50 to 85 Shore A, or in the range of 60 to 80 Shore A.

For closing the applicator 1, may be used a rinsing tip. The rinsing tip may be used for example during cleaning the applicator 1 and/or treatment liquid pipe 19 and/or vacuum pipe 18. The rinsing tip is adapted for attachment to the applicator 1, for example with a threaded connection. The rinsing tip may be attached to the applicator base 32. The rinsing tip may comprise the rim 25 and the closed top part for closing the liquid circuit comprising the treatment liquid container 12 or the rinsing fluid container 14, the main unit 8, the treatment liquid pipe 19, the applicator 1, the vacuum pipe 18 and the waste container 13.

The rinsing tip may be made from any appropriate material, for example from plastic or a polymer.

In one aspect of the invention, the applicator may be equipped with an adjustable liquid inflow regulation 29. The volume of treatment liquid consumed during therapy may be in the range of 20 to 1000 ml, or in the range of 30 to 500 ml, or in the range of 50 to 200 ml, or in the range of 70 to 90 ml.

Figure 15:
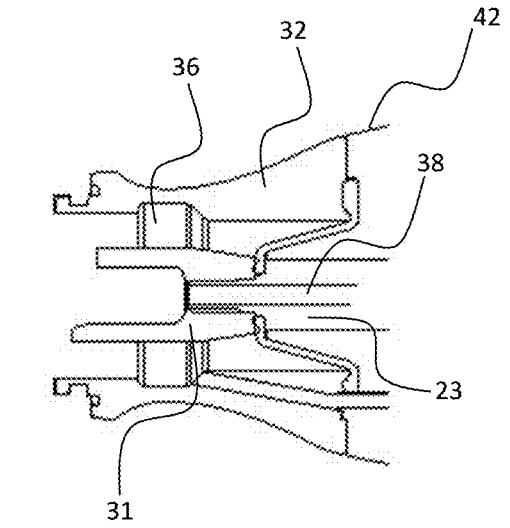

The arrangement of the applicator 1 for reducing spilling of serum is depicted in FIG. 15.

As it was already mentioned, one advantageous aspect of the invention is a design of the applicator 1 for reducing the risk of spilling treatment liquid (serum), especially when treatment is stopped or interrupted.

The applicator 1 may be equipped with a spilling reduction system 36, which forms a mechanical barrier preventing spilling of treatment liquid or rinsing fluid outside from the applicator 1. The spilling reduction system 36 may be in the form of a collar surrounding the tip base 31 in the applicator 1 and sealing the space around the tip base 31 in the area of the applicator base 32 connected to the applicator housing 42. The material from which the spilling reduction system 36 may be made, may include, but is not limited to, plastic material or metal.

The lowered pressure source 21 may be in the form of a vacuum pump. The requested lowered pressure for the therapy may be in the range of 5 to 90 kPa, or in the range of 12 to 50 kPa, or in the range of 15 to 30 kPa.

The power source 41 may be powered from a public electricity network e.g. power grid and/or power socket, the power source 41 may comprise at least one of a battery, a relay, a transformer, or a combination thereof, or other of standard power supplies.

The device may be optionally equipped with a heating/cooling system 40 for heating or cooling the treatment liquid or optionally for heating or cooling the rinsing fluid.

The heating/cooling system 40 may comprise heating/and cooling element, which may comprise a thermoelectric heater/cooler, for example a Peltier device, resistance heater, fan, or other similar appropriate device.

The requested temperature of the treatment liquid may be adjustable on the user interface 9 of the main unit 8, for example formed by display, or may be regulated manually on the main unit 8. The temperature of treatment liquid may be in the range of 18 to 50° C., or in the range of 20 to 45° C., or in the range of 30 to 40° C.

Figure 22:
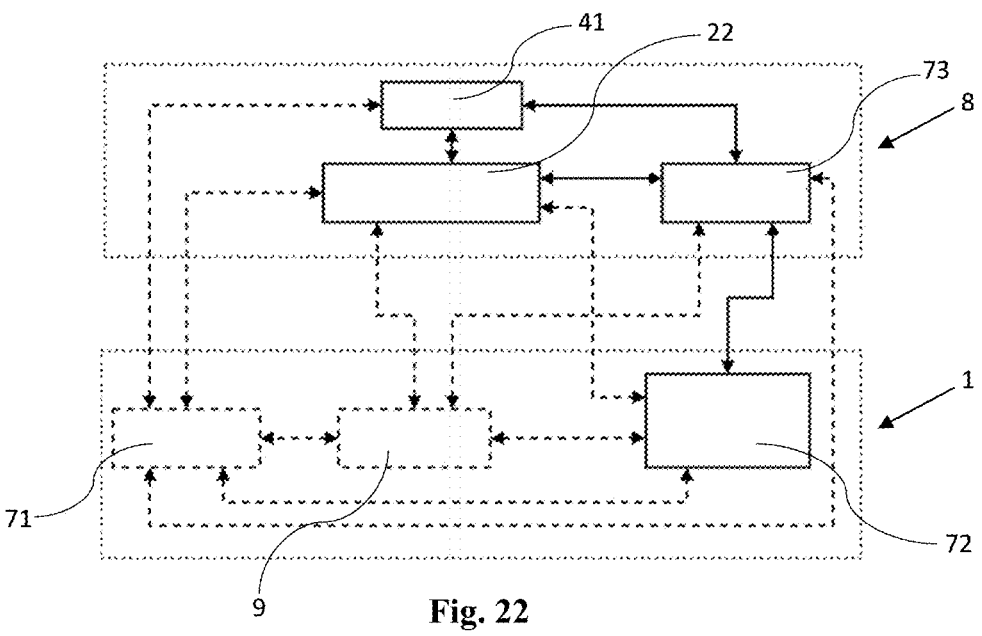

The applicator 1 may be equipped with a source of electromagnetic energy, for example RF energy. FIG. 22 shows a schematic view of one system for supplying electromagnetic energy through the applicator 1. The applicator 1 may be equipped with energy delivery element 72 which may comprise for example an RF electrode. The applicator 1 may be optionally equipped with a sensor 71 and user interface 9.

The sensor 71 may provide information about a physical quantity including energy, output of at least one energy delivery element 72, temperature of the treated tissue, temperature of the energy delivery element 72, or temperature of the heating/cooling media.

The sensor 71 may be connected to the central control unit 22.

A device according to the invention may include sensor 71 comprising a temperature sensor located on the applicator 1 and/or the applicator tip 2. The temperature sensor may include for example an IR sensor, a thermocouple, or the like. The method of treatment may include measurement of the temperature of tissue, for example temperature of treated skin. In addition, the method of treatment may include measurement of temperature of one or more energy delivery elements 72.

The main unit 8 may be equipped with the energy generator 73, for example high frequency generator and/or radiofrequency generator as a source of radiofrequency (RF) energy. The energy generator 73 may be connected to the power source 41 and the central control unit 22.

The frequency of radiofrequency energy may be in the range of 10 kHz to 300 GHz, or 300 kHz to 10 GHz, or 400 kHz to 6 GHz. In one narrower embodiment the frequency of radiofrequency energy may be in the range of 100 kHz to 550 MHz, or 250 kHz to 500 MHz, or 350 kHz to 100 Mhz, or 500 kHz to 80 MHz. In an even more specific embodiment, the frequency of the radiofrequency energy may be in the range of 250 kHz to 50 MHz, or 350 kHz to 10 MHz.

Output power of the radiofrequency energy may be less than or equal to 450, 300, 250 or 220 W. The radiofrequency energy may be applied in or close to the ISM bands of 6.78 MHz, 13.56 MHz, 27.12 MHz, 40.68 MHz, 433.92 MHz, 915 MHz, 2.45 GHz and 5.8 GHz. Radiofrequency energy may provide energy flux on the surface of the applicator and/or on the surface of the treated tissue (e.g. skin) in the range of $0.001 \ W \cdot cm^{-2}$ to $1500 \ W \cdot cm^{-2}$, or $0.01 \ W \cdot cm^{-2}$ to $1000 \ W \cdot cm^{-2}$, or $0.5 \ W \cdot cm^{-2}$ to $500 \ W \cdot cm^{-2}$. The radiofrequency energy may be applied in a monopolar, bipolar, unipolar and/or multipolar manner. Monopolar application of radiofrequency energy may include use of a neutral electrode in cooperation with an active RF electrode.

The temperature of tissue, skin and/or skin surface below the applicator 1 may be increased by application of targeted RF energy to a value in the range of 32° C. to 90° C., or 35° C. to 65° C., or 37° C. to 55° C., or 40° C. to 50° C.

Figure 20:
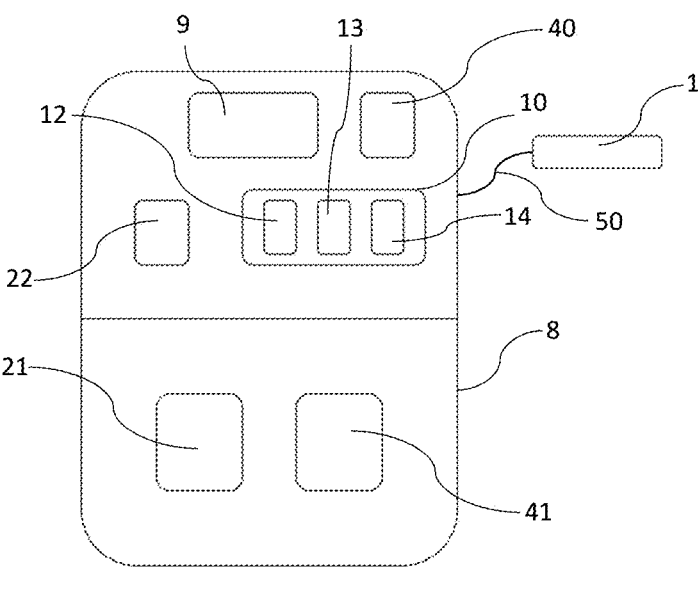
Figure 21:
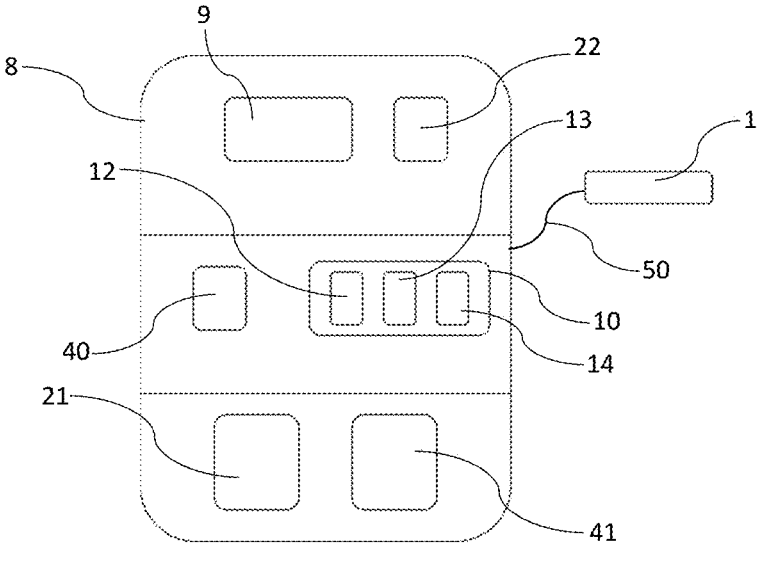

The components may be arranged in the main unit 8 as depicted in FIG. 20 and FIG. 21. One possible arrangement of the main components in the main unit 8 may be according to FIG. 20, where the main unit 8 is divided in two parts, upper and lower. The upper part of the main unit 8 may comprise the central control unit 22, the user interface 9, output of the connecting lumen 50 to the applicator 1, container's attachment 10, treatment liquid container 12, the waste container 13, the rinsing fluid container 14 and optionally the heating/cooling system 40, if applied.

The lower part of the main unit 8 may comprise for example the power source 41 and lowered pressure source 21, which may comprise vacuum pump 11.

Another possible arrangement of the main components in the main unit 8 may be as depicted in FIG. 21, where the main unit 8 is divided in three parts, upper, middle and lower. The upper part of the main unit 8 may comprise the central control unit 22 and the user interface 9. The middle part of the main unit 8 may comprise an output of the connecting lumen 50 to the applicator 1, container's attachment 10, treatment liquid container 12, the waste container 13, the rinsing fluid container 14 and optionally the heating/cooling system 40, if applied.

The lower part of the main unit 8 may comprise for example the power source 41 and lowered pressure source 21, which may comprise vacuum pump 11.

As mentioned above, the methods and the devices according to the invention effectively use the combination of mechanical cleansing strengthened by vibrations transmitted to at least a portion of the applicator tip 2, using lowered pressure and treatment liquid (serum).

The methods and the devices for performing the methods provide to the patient many benefits, which include in particular more efficient therapy, minimizing skin irritation and similar inconveniences. The therapy is safe and comfortable for the patient as well as for the person providing the therapy. Other advantages are transmitting vibrations directly to at least a portion of the applicator tip 2, which is in contact with the patient's skin. Vibrations of the whole applicator 1 are, in comparison with methods and devices according to the state of the art, significantly lowered, as are occurrence of hand pain and other inconveniences for the person providing the therapy.

Another advantageous aspect of the device is a special design of the applicator 1 for reducing risk of spilling of serum, when treatment is stopped or interrupted.

The invention claimed is:

1. A device for performing a skin treatment procedure, the device comprising:
an applicator comprising:
an applicator housing;
a tip base;
an applicator tip configured to be placed into the tip base, the applicator tip comprising at least one of a rim, a bristled tip, a solid tip, a lamellar tip, a rinsing tip, bristles, a rugged surface or a lamellar structure;
a vibration mechanism configured to create vibrations and comprising an electric rotary motor configured to provide rotational motion and an eccentric element configured to convert the rotational motion to a linear vibration movement in a direction perpendicular to a longitudinal axis of the applicator;
a transmission mechanism coupled to the vibration mechanism on one side and to the tip base on the other side, the transmission mechanism comprising:
a shaft configured to transmit vibrations to the tip base and the applicator tip; and
a fixing pin intersecting the shaft such that it defines an axis of rotation about which the shaft is configured for limited angular displacement;
wherein said displacement generates substantially linear motion of the shaft due to the eccentric loading imparted by the vibration mechanism; and
a vibration reducing element positioned between the vibration mechanism and the applicator housing, or positioned between the transmission mechanism and the applicator housing, configured to reduce vibrations of the applicator housing;
a main unit comprising:
a user interface;
a central control unit;
a lowered pressure source;
a container attachment;
a power source;
a treatment liquid container; and
a waste container; and
a connecting lumen configured to connect the main unit with the applicator;
wherein the main unit is configured to be in fluid communication with the applicator via the connecting lumen.

2. The device according to claim 1, wherein the electric rotary motor is configured to operate at a speed in a range of 1,500 to 60,000 rpm.

3. The device according to claim 1, wherein the position of the fixing pin along the shaft determines a length of a lever arm between a center of the fixing pin and an end of the shaft connected to the tip base, thereby influencing the amplitude and character of the motion transmitted to the applicator tip; and
wherein the length of the lever arm is in a range of 5 mm to 200 mm.

4. The device according to claim 1, wherein the device is configured to create vibrations of the applicator tip having a frequency in a range of 3,000 to 120,000 moves per minute.

5. The device according to claim 1, wherein the main unit comprises an upper part, a middle part and a lower part, wherein the upper part of the main unit comprises the central control unit and the user interface, the middle part of the main unit comprises the treatment liquid container and the waste container, and the lower part of the main unit comprises the power source and the lowered pressure source.

6. The device according to claim 1, wherein the container attachment is configured to connect the treatment liquid container and the waste container; and wherein the treatment liquid container or the waste container comprises a bottle having a volume in a range of 50 ml to 1000 ml.

7. The device according to claim 6, wherein the main unit further comprises a waste management system including the waste container, a valve, a vacuum pipe and a waste reservoir.

8. The device according to claim 7, wherein the waste container is configured to pour waste into the waste material reservoir via the valve; and wherein the waste reservoir is configured to be pulled out from the main unit.

9. A device for performing a skin treatment procedure, the device comprising:

an applicator comprising:

a tip base;

an applicator tip configured to be placed into the tip base, the applicator tip comprising at least one of a rim, a bristled tip, a solid tip, a lamellar tip, a rinsing tip, bristles, a rugged surface or a lamellar structure;

an electric rotary motor configured to provide rotational motion, and an eccentric element configured to convert the rotational motion to a linear vibration movement in a direction perpendicular to a longitudinal axis of the applicator;

a shaft coupled to the eccentric element on a first side and to the tip base on a second side opposite the first side, and configured to transmit vibrations to the tip base and the applicator tip, and a fixing pin intersecting the shaft such that it defines an axis of rotation about which the shaft is configured for limited angular displacement;

wherein said displacement generates substantially linear motion of the shaft due to the eccentric loading imparted by the eccentric element; and a main unit comprising:

a central control unit comprising a microprocessor and a memory, and comprising a stored software, data, protocols, or algorithms for controlling the skin treatment procedure;

a lowered pressure source; and a treatment liquid container; and a connecting lumen configured to connect the main unit with the applicator;

wherein the main unit is configured to be in fluid communication with the applicator via the connecting lumen.

10. The device according to claim 9, wherein the applicator further comprises an applicator housing and a vibration reducing element positioned between the applicator housing and at least one of the electric rotary motor, the eccentric element, the shaft, or the fixing pin, and configured to reduce vibrations of the applicator housing.

11. The device according to claim 10, wherein the vibration reducing element comprises a rubber or a silicone material.

12. The device according to claim 9, wherein the applicator tip comprises the solid tip configured to provide skin massage and enhancement of absorption of a protective substance to the skin; and wherein the solid tip comprises a rugged surface or a rugged surface pad with protrusions.

13. The device according to claim 12, wherein the solid tip comprises the rugged surface pad with protrusions, wherein the protrusions have a shape of a part of a sphere or have a hexagonal shape.

14. The device according to claim 12, wherein the solid tip comprises the rugged surface pad in a rounded diamond shape with hexagonal protrusions.

15. The device according to claim 9, wherein the applicator further comprises a treatment liquid pipe, a liquid inflow chamber and a treatment liquid cavity, configured to be coupled to the treatment liquid container via the connecting lumen, wherein the treatment liquid cavity is coupled to the applicator tip and is configured to provide a treatment liquid to the skin.

16. The device according to claim 15, wherein the applicator further comprises a spilling reduction system configured to prevent spilling of the treatment liquid from the applicator during an interruption or a termination of the treatment procedure.

17. A device for performing a skin treatment procedure, the device comprising:

an applicator comprising:

an applicator housing;

a tip base;

an applicator tip configured to be placed into the tip base, the applicator tip comprising at least one of a rim, a bristled tip, a solid tip, a lamellar tip, a rinsing tip, bristles, a rugged surface or a lamellar structure;

a vibration mechanism configured to create vibrations and comprising:

an electric rotary motor configured to provide rotational motion;

an eccentric element configured to convert the rotational motion to a linear vibration movement in a direction perpendicular to a longitudinal axis of the applicator; and a shaft bed;

a transmission mechanism comprising:

a shaft coupled to the eccentric element via the shaft bed on one side and to the tip base on the other side, and configured to transmit vibrations to the tip base and the applicator tip; and a fixing pin intersecting the shaft such that it defines an axis of rotation about which the shaft is configured for limited angular displacement;

wherein said displacement generates substantially linear motion of the shaft due to the eccentric loading imparted by the vibration mechanism; and a vibration reducing element positioned between the vibration mechanism and the applicator housing, or positioned between the transmission mechanism and the applicator housing, configured to reduce vibrations of the applicator housing.

18. The device according to claim 17, wherein the vibration reducing element comprises a rubber or a silicone material.

19. The device according to claim 17, wherein a length between a center of the fixing pin and an end of the shaft connected to the tip base is in a range of 5 mm to 200 mm.

20. The device according to claim 17, wherein a length between a center of the fixing pin and an end of the shaft connected to the eccentric element in a range of 5 mm to 200 mm.

21. The device according to claim 17, wherein the limited angular displacement is in a range of 0.01 degrees to 20 degrees.

22. The device according to claim 17, wherein the device is configured to create vibrations of the applicator tip having a frequency in a range of 3,000 to 120,000 moves per minute.

23. The device according to claim 17, wherein the applicator tip comprises the bristle tip having a length of bristles in a range of 2 mm to 25 mm.

24. The device according to claim 17, further comprising:
a main unit comprising:
a central control unit; and
a treatment liquid container; and
a connecting lumen configured to connect the main unit with the applicator;
wherein the main unit is configured to provide a treatment liquid from the treatment liquid container to the applicator via the connecting lumen.

25. A device for performing a skin treatment procedure, the device comprising:
an applicator comprising:
an applicator housing;
a tip base;
an applicator tip configured to be placed into the tip base;
a vibration mechanism configured to create vibrations and comprising an electric rotary motor configured to provide rotational motion and an eccentric element configured to convert the rotational motion to a linear vibration movement in a direction perpendicular to a longitudinal axis of the applicator;
a transmission mechanism coupled to the vibration mechanism on one side and to the tip base on the other side, the transmission mechanism comprising:
a shaft configured to transmit vibrations to the tip base and the applicator tip; and
a fixing pin intersecting the shaft so that it defines an axis of rotation about which the shaft is configured for limited angular displacement;
wherein said displacement generates substantially linear motion of the shaft due to the eccentric loading imparted by the vibration mechanism; and
a treatment liquid pipe, a liquid inflow chamber and a treatment liquid cavity coupled to the applicator tip and configured to provide a treatment liquid to the skin; and
a vacuum pipe configured to remove waste material from the skin; and
a main unit comprising:
a central control unit comprising software, data, protocols, or algorithms for controlling the procedure;
a lowered pressure source;

a treatment liquid container configured to store the treatment liquid;
a waste container coupled to the lowered pressure source and configured to collect removed waste material from the skin; and
a container attachment configured to connect the treatment liquid container and the waste container; and
a connecting lumen comprising the treatment liquid pipe and the vacuum pipe;
wherein the connecting lumen is configured to connect the main unit with the applicator;
wherein the treatment liquid container is coupled with the treatment liquid pipe, and
wherein the waste container is coupled with the vacuum pipe.

26. The device according to claim 25, wherein the main unit further comprises:
a rinsing fluid container configured to store a rinsing fluid; and
a switching system configured to switch between coupling the applicator with the treatment liquid container or the rinsing fluid container; and
wherein the container attachment is further configured to connect the rinsing fluid container.

27. The device according to claim 25, wherein the treatment liquid container or the waste container comprises a bottle having a volume in a range of 50 ml to 1000 ml.

28. The device according to claim 25, wherein the container attachment comprises a container fixing mechanism comprising:
a fixing base configured to receive at least a portion of the treatment liquid container;
one or more balls positioned within the fixing base; and
one or more springs, each spring configured to apply pressure on one of the balls;
wherein the balls are configured to exert a radial force against the treatment liquid container when inserted into the fixing base; and
wherein the treatment liquid container comprises a retention feature configured to cooperate with the radial force of the balls to retain the container within the fixing base.

29. The device according to claim 28, wherein the retention feature comprises at least one of a thread, a collar, or an O-ring.

30. The device according to claim 25, wherein the lowered pressure source comprises a vacuum pump configured to provide lowered pressure for the treatment procedure in a range of 5 kPa to 90 kPa.

* * * * *